United States Patent [19]

Lindner et al.

[11] Patent Number: 4,929,642
[45] Date of Patent: May 29, 1990

[54] PEST-COMBATING AGENTS BASED ON SUBSTITUTED 1,4-NAPHTHOQUINONES AND NEW SUBSTITUTED 1,4-NAPHTHOQUINONES

[75] Inventors: Werner Lindner, Cologne; Benedikt Becker, Mettmann; Robert Steffens, Cologne; Ulrike Wachendorff-Neumann, Leverkusen; Wilhelm Brandes, Leichlingen; Wilhelm Stendel, Wuppertal; Stefan Dutzmann, Duesseldorf, all of Fed. Rep. of Germany

[73] Assignee: Bayer Aktiengesellschaft, Leverkusen, Fed. Rep. of Germany

[21] Appl. No.: 212,816

[22] Filed: Jun. 29, 1988

[30] Foreign Application Priority Data

Jul. 3, 1987 [DE] Fed. Rep. of Germany ....... 3722018
Jan. 22, 1988 [DE] Fed. Rep. of Germany ....... 3801743

[51] Int. Cl.$^5$ .......................... A01N 9/00; A01N 9/24
[52] U.S. Cl. ................................... 514/510; 514/529; 514/532; 514/543; 514/544; 514/682; 552/298; 552/299; 71/103; 71/108; 71/122; 71/123
[58] Field of Search ................. 260/396 R; 514/682, 514/545, 709, 521, 529, 530, 532, 543, 510; 71/123, 103, 108, 122

[56] References Cited

U.S. PATENT DOCUMENTS

| | | | |
|---|---|---|---|
| 2,553,647 | 5/1951 | Fieser et al. | 260/396 |
| 3,673,222 | 6/1972 | Archer et al. | 260/396 R |
| 4,053,634 | 10/1977 | Bellina et al. | 424/312 |
| 4,055,661 | 10/1977 | Bellina et al. | 424/311 |
| 4,070,481 | 1/1978 | Bellina et al. | 260/396 R |
| 4,110,473 | 7/1978 | Fugitt et al. | 424/33 |
| 4,143,157 | 3/1979 | Bellina et al. | 424/314 |

FOREIGN PATENT DOCUMENTS 0123238 10/1984 European Pat. Off. .
7107128 12/1971 France .

OTHER PUBLICATIONS

Pestic. Sci. 4 (1973), pp. 193–200.
Liebigs Ann. Chem. 763 (1972), pp. 135–147.
J. Am. Che. Soc. 58 (1936), pp. 1163–1167, ibid 70 (1948), pp. 3165–3174 and ibid. 70 (1948), pp. 3174–3175, ibid 74 (1952), pp. 3910–3915.
J. Chem. Soc. 1935, pp. 1850–1854.

Primary Examiner—Richard L. Raymond
Assistant Examiner—Raymond Covington
Attorney, Agent, or Firm—Sprung Horn Kramer & Woods

[57] ABSTRACT

A method of combating agricultural pest comprising applying a pesticidally effective amount of a substituted 1,4-naphthoquinone on agricultural pests and/or their environment, said 1,4-naphthoquinone being of the formula

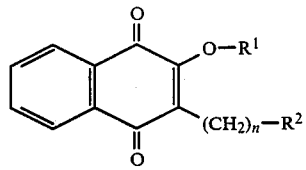

in which
n represents the number zero or a number from 1 to 12,
$R^1$ represents hydrogen, t-butylcarbonyl or acetyl and
$R^2$ represents phenyl which is substituted by bromine, fluorine, chlorine, trifluoromethyl, trifluoromethoxy, trifluoromethylsulphenyl, trifluoromethylsulphonyl or trimethylsilyl or cyclohexyl which is substituted by methyl, trifluoromethyl or trimethylsilyl or
$R^2$ represents $C_1$–$C_8$-alkyl which is substituted by fluorine, chlorine or bromine.

6 Claims, No Drawings

PEST-COMBATING AGENTS BASED ON SUBSTITUTED 1,4-NAPHTHOQUINONES AND NEW SUBSTITUTED 1,4-NAPHTHOQUINONES

The invention relates to the use of substituted 1,4-naphthoquinones, some of which are known, as agents for combating pests, in particular as acaricides and fungicides, and to new substituted 1,4-naphthoquinones and processes for their preparation.

It is known that certain substituted 1,4-naphthoquinones, such as, for example, 2-nonyl-, 2-decyl- and 2-(3-cyclohexyl-propyl)-3-hydroxy-1,4-naphthoquinone, have insecticidal and acaricidal properties (compare U.S. Pat. No. 2,572,946).

A fungicidal action of such compounds has also been disclosed (compare Pestic. Sci. 4 (1973), 193–200). However, the action of these compounds is not always satisfactory, especially in the case of low application rates and/or concentrations of active compound.

It is also known that certain substituted 1,4-naphthoquinones which contain specific cycloalkyl groups can be used against Protozoa on stock animals (compare European Patent A-2,228, European Patent A-77,550, European Patent A-77,551, European Patent A-123,238 and European Patent A-123,239). However, nothing is as yet known of a use of such compounds in plant protection, for example, as acaricides or as fungicides.

It has now been found that the substituted 1,4-naphthoquinones, some of which are known, of the general formula (I)

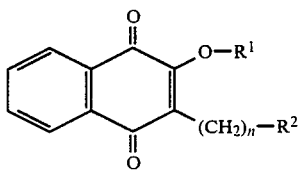

in which
n represents the number zero or a number from 1 to 12,
$R^1$ represents hydrogen, or represents an optionally substituted radical R from the series comprising alkyl, aralkyl, alkylcarbonyl, alkoxycarbonyl, alkylsulphonyl and arylsulphonyl and
$R^2$ represents halogenoalkyl, optionally substituted aryl or substituted cycloalkyl,
have a powerful action as agents for combating pests, in particular as acaricides and as fungicides.

Surprisingly, the substituted 1,4-naphthoquinones of the general formula (I) exhibit a more powerful acaricidal and fungicidal action than the abovementioned known compounds of similar structure.

The invention preferably relates to the use of agents for combating pests and pest-combating agents, in particular acaricides and fungicides, based on compounds of the general formula (I), in which n represents the number zero, 1 or 2,
$R^1$ represents hydrogen, or represents a radical R which is optionally substituted as described below and is chosen from the series comprising $C_1$–$C_{12}$-alkyl (which is optionally substituted by fluorine, chlorine or $C_3$–$C_6$-cycloalkyl), benzyl (which is optionally substituted by fluorine, chlorine or bromine), $C_1$–$C_{12}$-alkylcarbonyl (which is optionally substituted by fluorine, chloride, bromine, phenyl, $C_1$–$C_2$-alkoxy or $C_3$–$C_6$-cycloalkyl), $C_1$–$C_4$-alkoxy-carbonyl, $C_1$–$C_8$-alkylsulphonyl (which is optionally substituted by fluorine or chlorine) and phenylsulphonyl and naphthylsulphonyl (which are optionally substituted by fluorine, chlorine, bromine, cyano, nitro, $C_1$–$C_4$-alkyl, trifluoromethyl, $C_1$–$C_4$-alkoxy, $C_1$–$C_4$-alkylsulphonyl, dimethylaminosulphonyl and/or $C_1$–$C_4$-alkoxycarbonyl); and
$R^2$ represents $C_1$–$C_8$-alkyl, which is substituted by fluorine and/or chlorine, phenyl which is optionally substituted by fluorine, chlorine, bromine, cyano, nitro, $C_1$–$C_6$-alkyl, trifluoromethyl, $C_1$–$C_4$-alkoxy, $C_1$–$C_2$-fluoroalkoxy, $C_1$–$C_4$-alkylthio, $C_1$–$C_2$-fluoroalkylthio, $C_1$–$C_4$-alkylsulphinyl, $C_1$–$C_2$-fluoroalkylsulphinyl, $C_1$–$C_4$-alkylsulphonyl, $C_1$–$C_2$-fluoroalkylsulphonyl and or tri-($C_1$–$C_2$-alkyl)-silyl or cyclohexyl which is substituted by $C_1$–$C_6$-alkyl, trifluoromethyl and/or tri-($C_1$–$C_2$-alkyl)-silyl.

Compounds of the formula (I) which are particularly preferably used according to the invention are those in which
n represents the numbers zero, 1 or 2,
$R^1$ represents hydrogen, methyl or acetyl and
$R^2$ represents phenyl which is substituted by fluorine, chlorine, $C_1$–$C_4$-alkyl, trifluoromethyl, $C_1$–$C_3$-alkoxy, trifluoromethoxy, $C_1$–$C_3$-alkylthio, trifluoromethylsulphenyl, $C_1$–$C_3$-alkylsulphinyl, trifluoromethylsulphinyl, $C_1$–$C_3$-alkylsulphonyl, trifluoromethylsulphonyl or trimethylsilyl, or cyclohexyl which is substituted by $C_1$–$C_4$-alkyl, trifluoromethyl or trimethylsilyl.

Examples which may be mentioned of the compounds of the formula (I) to be used according to the invention are: 2-(4-tert.-butyl-cyclohexyl)-3-hydroxy-1,4-naphthoquinone, 2-(4-trimethylsilyl-cyclohexyl)-3-hydroxy-1,4-naphthoquinone, 2-(3-trifluoromethyl-1-cyclohexyl-methyl)-3-hydroxy-1,4-naphthoquinone, 2-(4-trifluoromethyl-1-cyclohexyl-methyl)-3-hydroxy-1,4-naphthoquinone, 2-(2-(4-trifluoromethyl-1-cyclohexyl)-ethyl)-3-hydroxy-1,4-naphthoquinone, 2-(3-trifluoromethyl-1-cyclohexyl-methyl)-3-acetoxy-1,4-naphthoquinone, 2-(3-trifluoromethylphenyl-methyl)-3-hydroxy-1,4-napthoquinone and 2-(2-(4-trifluoromethylthio-phenyl)-ethyl-3-hydroxy-1,4-naphthoquinone.

These compounds are especially preferred because of their outstanding acaricidal and fungicidal action.

Examples of the compounds of the formula (I) to be used according to the invention are furthermore listed in the following Table 1.

TABLE 1
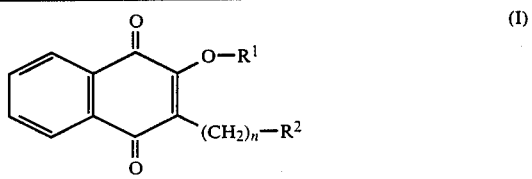
Examples of compounds of the formula (I)
| Example No. | $R^1$ | $R^2$ | n | Melting point (°C.) |
|---|---|---|---|---|
| 1 | H | ‑⟨H⟩‑C(CH$_3$)$_3$ (cyclohexyl) | 0 | 95 |
| 2 | H | ‑⟨H⟩‑CF$_3$ (cyclohexyl, meta) | 1 | 142 |
| 3 | H | ‑⟨H⟩‑CF$_3$ (cyclohexyl) | 1 | 125 |
| 4 | H | ‑⟨H⟩‑CF$_3$ (cyclohexyl) | 2 | 115 |
| 5 | H | ‑⟨H⟩‑Si(CH$_3$)$_3$ (cyclohexyl) | 0 | 65 |
| 6 | H | ‑⟨phenyl⟩‑CF$_3$ (meta) | 1 | 158 |
| 7 | H | ‑⟨phenyl⟩‑SCF$_3$ (para) | 2 | 118 |
| 8 | H | CF$_3$ | 2 | 140 |
| 9 | —CO—CH$_3$ | ‑⟨H⟩‑CF$_3$ (cyclohexyl) | 1 | 110 |
| 10 | —CO—OCH$_3$ | ‑⟨H⟩‑CF$_3$ (cyclohexyl) | 1 | 114 |

TABLE 1-continued
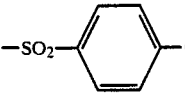
(I)
Examples of compounds of the formula (I)
| Example No. | R¹ | R² | n | Melting point (°C.) |
|---|---|---|---|---|
| 11 | 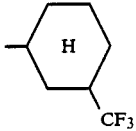 | 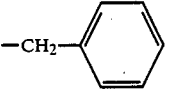 | 1 | 116 |
| 12 | 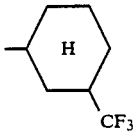 | 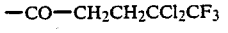 | 1 | 100 |
| 13 | —CO—CH₂CH₂CCl₂CF₃ | 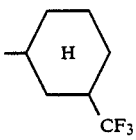 | 1 | (amorph) |
| 14 | —CO—CH₃ | 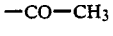 | 0 | 110 |
| 15 | —CH₃ | 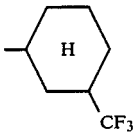 | 1 | 90 |
| 16 | —CO—CH₃ |  | 1 | 108 |
| 17 | —CO—CH₃ | 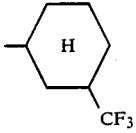 | 2 | 105 |
| 18 | —CO—CH₃ | CF₃ | 2 | 105 |
| 19 | —SO₂—CH₃ |  | 1 | |
| 20 | —CO—CH₂Cl | 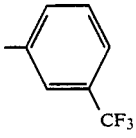 | 1 | |

TABLE 1-continued

Examples of compounds of the formula (I)

$$\text{(I)}$$

Structure: naphthoquinone with O—R¹ at position 2 and (CH₂)ₙ—R² at position 3.

| Example No. | R¹ | R² | n | Melting point (°C.) |
|---|---|---|---|---|
| 21 | —CO—CHCl₂ | 4-(CF₃)-cyclohexyl (H shown) | 1 | |
| 22 | —SO₂CF₃ | 3-(CF₃)-cyclohexyl (H shown) | 1 | |
| 23 | —C(=O)—(CH₂)₇CH₃ | 3-(CF₃)-cyclohexyl (H shown) | 1 | |
| 24 | H | 4-Cl-phenyl | 2 | |
| 25 | H | 3-Cl-phenyl | 2 | |
| 26 | H | 2-Cl-phenyl | 2 | 171 |
| 27 | H | phenyl | 2 | 177 |
| 28 | H | 4-CH₃-phenyl | 1 | 168 |
| 29 | H | 4-CH₃-phenyl | 2 | |

TABLE 1-continued

Examples of compounds of the formula (I)

$$\text{(I)}$$

Structure: 1,4-naphthoquinone with $O-R^1$ at 2-position and $(CH_2)_n-R^2$ at 3-position.

| Example No. | $R^1$ | $R^2$ | n | Melting point (°C.) |
|---|---|---|---|---|
| 30 | H | 2-methylphenyl (o-CH₃-C₆H₄-) | 2 | |
| 31 | H | 4-methoxyphenyl (p-CH₃O-C₆H₄-) | 2 | |
| 32 | H | 4-tert-butylphenyl (p-(CH₃)₃C-C₆H₄-) | 2 | |
| 33 | —C(=O)—CH₃ | 4-chlorophenyl (p-Cl-C₆H₄-) | 2 | |
| 34 | —C(=O)—CH₃ | phenyl (C₆H₅-) | 2 | 93 |
| 35 | —C(=O)—CH₃ | 4-methylphenyl (p-CH₃-C₆H₄-) | 2 | |
| 36 | —CH₃ | 4-chlorophenyl (p-Cl-C₆H₄-) | 2 | |
| 37 | —CH₃ | 4-methylphenyl (p-CH₃-C₆H₄-) | 2 | |
| 38 | —CH₂—C₆H₅ | 4-chlorophenyl (p-Cl-C₆H₄-) | 2 | |
| 39 | H | —(CH₂)₇—CF₃ | 1 | |
| 40 | —C(=O)—CH₃ | —(CH₂)₇—CF₃ | 1 | |
| 41 | —CH₃ | —(CH₂)₇—CF₃ | 1 | |
| 42 | —CH₂—C₆H₅ | —(CH₂)₇—CF₃ | 1 | |

TABLE 1-continued $$\text{(I)}$$

Structure: Naphthoquinone with O—R¹ at 2-position and (CH₂)ₙ—R² at 3-position.

Examples of compounds of the formula (I)

| Example No. | R¹ | R² | n | Melting point (°C.) |
|---|---|---|---|---|
| 43 | —SO₂—C₆H₄—CH₃ (p-tolyl) | —(CH₂)₇—CF₃ | 1 | |
| 44 | H | 2-(CF₃)-phenyl | 2 | 105 |
| 45 | H | 2-(CF₃)-cyclohexyl | 2 | 88 |
| 46 | —CO—CH₃ | 4-(CF₃)-phenyl | 1 | 160 |
| 47 | —CO—CH₃ | 2-Cl-phenyl | 2 | 90 |
| 48 | —CO—CH₃ | 4-CH₃-phenyl | 1 | 92 |
| 49 | H | 3,5-bis(CF₃)-phenyl | 2 | 142 |
| 50 | H | 3,5-bis(CF₃)-cyclohexyl | 2 | 120 |
| 51 | —CO—CH₃ | 3,5-bis(CF₃)-cyclohexyl | 2 | |

TABLE 1-continued

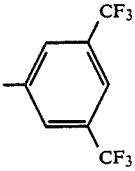

Examples of compounds of the formula (I)

| Example No. | R¹ | R² | n | Melting point (°C.) |
|---|---|---|---|---|
| 52 | —CO—CH₃ | 3,5-bis(CF₃)-phenyl | 2 | |
| 53 | —CO—CH₃ | 3-CF₃-cyclohexyl | 2 | |
| 54 | —CO—CH₃ | 3-CF₃-phenyl | 2 | |

The compounds of the formula (I) are known and/or can be prepared by processes which are known per se (compare Liebigs Ann. Chem. 763 (1972), 135–147; Acta Chem. Scand. 27 (1973), 6; J. Am. Chem. Soc. 58 (1936), 1163–1167; ibid. 70 (1948), 3165–3173; ibid. 70 (1948), 3174–3175; ibid. 74 (1952), 3910–3915; DE-OS (German Published Specification) 2,641,343; European Patent A-2,228; European Patent A-77,550; European Patent A-77,551; European Patent A-123,238; European Patent A-123,239; British Patent Specification 1,553,424; U.S. Pat. No. 2,553,648; U.S. Pat. No. 3,367,830 and U.S. Pat. No. 3,347,742).

The present invention furthermore relates to new substituted 1,4-naphthoquinones of the general formula (Ia)

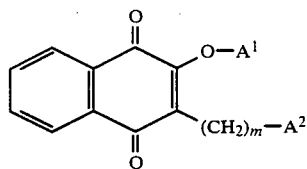

in which
m represents the number 0 or a number from 1 to 12,
A¹ represents hydrogen, methyl, benzyl, acetyl, methoxycarbonyl, benzenesulphonyl or toluenesulphonyl and
A² represents trifluoromethyl, 3-trifluoromethylcyclohexyl, 3-trifluoromethyl-phenyl, 4-trimethylsilyl-cyclohexyl or 4-trifluoromethylthiophenyl
with the proviso that m is other than 0 and 2 if A² represents 3-trifluoromethyl-cyclohexyl or 3fluoromethylphenyl.

The new compounds of the formula (Ia) are obtained by a process in which
(a) 2-substituted 3-halogeno-1,4-naphthoquinones of the general fromula (II)

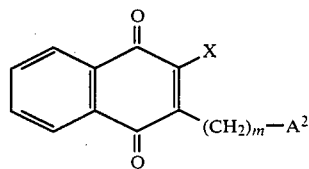

in which
m and A² have the abovementioned meanings and
X represents halogen,
are reacted with an alkali metal hydroxide or alkaline earth metal hydroxide, if appropriate in the presence of a diluent, or (b) 2,3-epoxy-2,3-dihydro-1,4-naphthoquinones of the general formula (III)

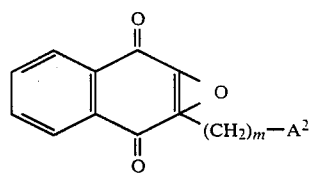

in which
m and A² have the abovementioned meanings,
are reacted with an alkali metal hydroxide or alkaline earth metal hydroxide, if appropriate in the presence of a diluent, or (c) 2-substituted 3-hydroxy-1,4-naphthoquinones of the general formula (Ib)

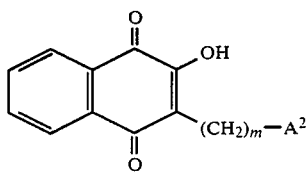
(Ib)

in which
m and $A^2$ have the abovementioned meanings,
are reacted with compounds of the general formula (IV)

$$Y - A \qquad (IV)$$

in which
A has the meaning given above for $A^1$, with the exception of hydrogen, and
Y represents a nucleofugic leaving group,
if appropriate in the presence of a metal salt, if appropriate in the present of an acid acceptor and if appropriate in the presence of a diluent.

Preferred new substituted 1,4-naphthoquinones of the formula (Ia) are those in which
  m represents the number zero or a number from 1 to 10,
  $A^1$ represents hydrogen, methyl, acetyl or benzyl and
  $A^2$ represents trifluoromethyl, 3-trifluoromethylcyclohexyl, 3-trifluoromethyl-phenyl, 4-trifluoromethylsilyl-cyclohexyl or 4-trifluoromethylthio-phenyl
with the proviso that m is other than zero and 2 if $A^2$ represents 3-trifluoromethyl-cyclohexyl or 3-trifluoromethyl-phenyl.

If, for example, 3-bromo-2-(3-trifluoromethyl-phenyl)-ethyl)-1,4-naphthoquinone and potassium hydroxide are used as starting substances in process variant (a) according to the invention for the preparation of the new compounds of the formula (Ia), the course of the reaction can be outlined by the following equation:

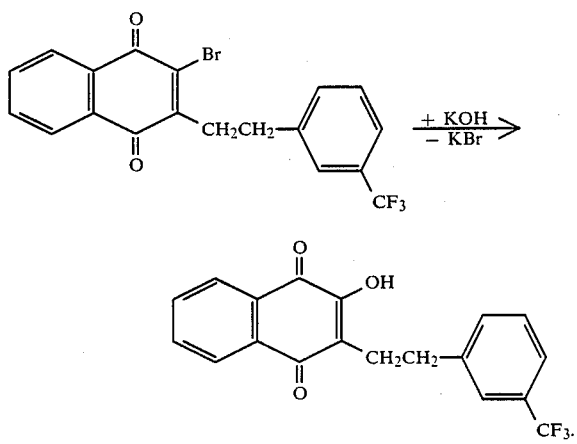

If, for example, 2,3-epoxy-2,3-dihydro-2-(4-trimethylsilyl-cyclohexyl-methyl)-1,4-naphthoquinone and sodium hydroxide are used as starting substances in process variant (b) according to the invention, the course of the reaction can be outlined by the following equation:

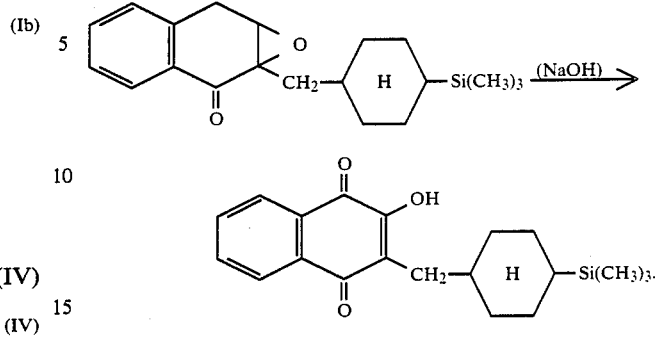

If, for exmaple, 3-hydroxy-2-(2,2,2-trifluoroethyl)-1,4-naphthoquinone and methyl bromide are used as starting substances in process variant (c) according to the invention, the course of the reaction can be outlined by the following equation:

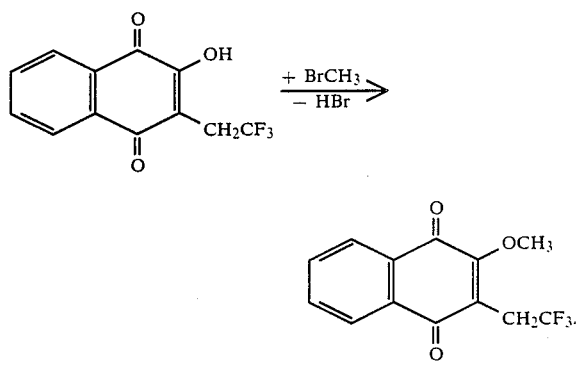

Formula (II) provides a general definition of the 2-substituted 3-halogeno-1,4-naphthoquinones to be used as starting substances in process variant (a). In formula (II), m and $A^2$ preferably have the same meanings as are given above as preferred for m and $A^2$ in the description of the new active compounds of the formula (Ia), and X preferably represents chlorine or bromine.

Examples of the new starting substances of the formula (II) are listed in the following Table 2.

TABLE 2

Examples of compounds of the formula (I))

| Example No. | X | m | $A^2$ | Melting point (°C.) |
|---|---|---|---|---|
| II-1 | Cl | 1 | cyclohexyl-H/CF3 | 104 |
| II-2 | Br | 2 | CF3 | |
| II-3 | Cl | 3 | CF3 | |

TABLE 2-continued

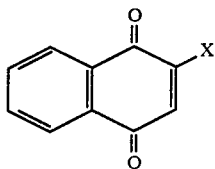

(II)

Examples of compounds of the formula (I)

| Example No. | X | m | A² | Melting point (°C.) |
|---|---|---|---|---|
| II-4 | Br | 2 | 4-(CF₃)-cyclohexyl (H) | |
| II-5 | Cl | 1 | 3-(CF₃)-phenyl | |
| II-6 | Cl | 0 | 4-Si(CH₃)₃-cyclohexyl (H) | |
| II-7 | Br | 1 | 4-Si(CH₃)₃-cyclohexyl (H) | |
| II-8 | Cl | 0 | 3-(CF₃)-phenyl | |
| II-9 | Cl | 0 | 4-(SCF₃)-phenyl | |
| II-10 | Cl | 1 | 4-(SCF₃)-phenyl | |
| II-11 | Cl | 2 | 4-(SCF₃)-phenyl | |

The starting substances of the formula (II) are not yet known from the literature. The new 2-substituted 3-halogeno-1,4-naphthoquinones of the formula (II) are obtained by a process in which 2-halogeno-1,4-naphthoquinones of the formula (V)

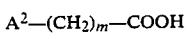

in which
X has the abovementioned meaning,
are reacted with carboxylic acids of the formula (VI)

$$A^2-(CH_2)_m-COOH \qquad (VI)$$

in which
m and A² have the abovementioned meanings,
in the presence of silver nitrate and ammonium peroxodisulphate and in the presence of a diluent, such as, for example, acetonitrile, water and sulpholane, at temperatures between 0° C. and 100° C., preferably between 10° C. and 80° C.

Formula (V) provides a general definition of the 2-halogeno-1,4-naphthoquinones to be used as intermediate products. In formula (V), X preferably represents chlorine or bromine.

Examples which may be mentioned of the compounds of the formula (V) are: 2-chloro-1,4-naphthoquinone and 2-bromo-1,4-naphthoquinone.

The compounds of the formula (V) are known (compare J. Chem. Soc. 1935, 1850–1854).

Formula (VI) provides a general definition of the carboxylic acids furthermore to be used as intermediate products. In formula (VI), m and A² preferably have the same meanings as are given above as preferred for m and A² in the description of the new active compounds of the formula (Ia).

Examples which may be mentioned of the compounds of the formula (VI) are: 3-trifluoromethyl-benzoic acid, (3-trifluoromethyl-phenyl)-acetic acid, ω-(3-trifluoromethyl-phenyl)-propionic acid, 3-trifluoromethyl-cyclohexane-carboxylic acid, (3-trifluoromethyl-cyclohexyl)-acetic acid, ω-(3-trifluoromethyl-cyclohexyl)-propionic acid, 4-trimethylsilyl-cyclohexane-carboxylic acid, (4-trimethylsilyl-cyclohexyl)-acetic acid, ω-(4-trimethylsilyl-cyclohexyl)-propionic acid, 4-trifluoromethylthiobenzoic acid, (4-trifluoromethylthio-phenyl)-acetic acid and ω-(4-trifluoromethyl-phenyl)-propionic acid.

The compounds of the formula (VI) are known and-/or can be prepared by processes which are known per se (compare European Patent A-2,228, European Patent A-77,550, European Patent A-77,551 and European Patent A-123,238). For example, the compounds of the formula (VI) in which A² represents 3-trifluoromethyl-cyclohexyl or 4-trimethylsilyl-cyclohexyl are obtained by a process in which the corresponding compounds of the formula (VI) in which A² represents 3-trifluoromethylphenyl or 4-trimethylsilyl-phenyl are hydrogenated by customary methods, for example, in the presence of rhodium catalysts or ruthenium catalysts (compare P. N. Rylander, Catalytic Hydrogenation in Organic Syntheses, Academic Press, Now York 1979).

Formula (III) provides a general definition of the 2,3-epoxy-2,3-dihydro-1,4-naphthoquinones to be used as starting substances in process variant (b). In formula (III), m and A² preferably have the same meanings as are given above as preferred for m and A² in the description of the new active compounds of the formula (Ia).

Examples of the new starting substances of the formula (III) are listed in the following Table 3.

TABLE 3

(III)

Examples of compounds of the formula (III)

| Example No. | m | A² | Melting point (°C.) |
|---|---|---|---|
| III-1 | 1 | —⟨H⟩—CF₃ (cyclohexyl) | 85 |
| III-2 | 2 | —⟨phenyl⟩—CF₃ | |
| III-3 | 2 | CF₃ | |
| III-4 | 3 | CF₃ | |
| III-5 | 2 | —⟨H⟩—CF₃ (cyclohexyl) | |
| III-6 | 1 | —⟨phenyl⟩—CF₃ | |
| III-7 | 0 | —⟨H⟩—Si(CH₃)₃ (cyclohexyl) | |
| III-8 | 1 | —⟨H⟩—Si(CH₃)₃ (cyclohexyl) | |
| III-9 | 0 | —⟨phenyl⟩—CF₃ | |
| III-10 | 0 | —⟨phenyl⟩—SCF₃ | |

TABLE 3-continued (III)

Examples of compounds of the formula (III)

| Example No. | m | A² | Melting point (°C.) |
|---|---|---|---|
| III-11 | 1 | —⟨phenyl⟩—SCF₃ | |
| III-12 | 2 | —⟨phenyl⟩—SCF₃ | |

The starting substances of the formula (III) are not yet knonw from the literature. The new 2,3-epoxy-2,3-dihydro-1,4-naphthoquinones of the formula (II) are obtained by a process in which 2-substituted 1,4-naphthoquinones of the formula (VII)

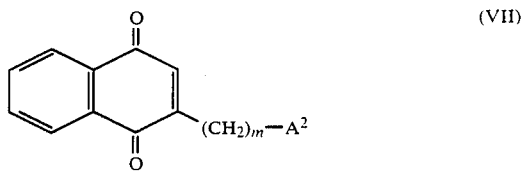

(VII)

in which m and A² have the abovementioned meanings, are reacted with hydrogen peroxide in the presence of a diluent, such as, for example, water and dioxane, and if appropriate in the presence of an acid acceptor, such as, for example, sodium carbonate or potassium carbonate, at temperatures between 0° C. and 100° C., preferably between 10° C. and 80° C.

Formula (VII) provides a general definition of the 2-substituted 1,4-naphthoquinones to be used as intermediate products.

In formula (VII), m and A² preferably have the same meanings as are given above as preferred for m and A² in the description of the new active compounds of the formula (Ia).

Examples of the new intermediate products of the formula (VII) are listed in the following Table 4.

TABLE 4

$$\text{(VII)}$$

1,4-naphthoquinone with $-(CH_2)_m-A^2$ substituent at 2-position

Examples of compounds of the formula (VII)

| Example No. | m | $A^2$ | Melting point (°C.) |
|---|---|---|---|
| VII-1 | 1 | 4-CF$_3$-cyclohexyl | 65 |
| VII-2 | 2 | 3-CF$_3$-phenyl | |
| VII-3 | 2 | CF$_3$ | |
| VII-4 | 3 | CF$_3$ | |
| VII-5 | 2 | 4-CF$_3$-cyclohexyl | |
| VII-6 | 1 | 3-CF$_3$-phenyl | |
| VII-7 | 0 | 4-Si(CH$_3$)$_3$-cyclohexyl | |
| VII-8 | 1 | 4-Si(CH$_3$)$_3$-cyclohexyl | |
| VII-9 | 0 | 3-CF$_3$-phenyl | |
| VII-10 | 0 | 4-SCF$_3$-phenyl | |
| VII-11 | 1 | 4-SCF$_3$-phenyl | |
| VII-12 | 2 | 4-SCF$_3$-phenyl | |

The intermediate products of the formula (VII) are not yet known from the literature. The new 2-substituted 1,4-naphthoquinones of the formula (VII) are obtained by a process in which 1,4-naphthoquinone is reacted with carboxylic acids of the formula (VI)—see above—in the presence of silver nitrate and ammonium peroxodisulphate and in the presence of a diluent, such as, for example, acetonitrile and water, at temperatures between 0° C. and 100° C., preferably between 10° C. and 80° C.

Reference is made to the above statements in respect of the carboxylic acids of the formula (VI).

Formula (Ib) provides a general definition of the 2-substituted-3-hydroxy-1,4-naphthoquinones to be used as starting substances in process variant (c). In formula (Ib), m and $A^2$ preferably have the same meanings as are given above as preferred for m and $A^2$ in the description of the new active compounds of the formula (Ia).

Examples of compounds of the formula (Ib) are to be found in Table 1 (Example 2, 5, 6, 7 and 8).

The 2-substituted 3-hydroxy-1,4-napthoquinones of the formula (Ib) are new compounds according to the invention which can be prepared by process variants (a) and (b).

Formula (IV) provides a general definition of the compounds furthermore to be used as starting substances in process variant (c). The nucleofugic leaving group Y in formula (IV) is preferably halogen. In formula (IV), in particular, $A^1$ represents methyl or acetyl and
Y represents chlorine, bromine or iodine.

Examples which may be mentioned of the compounds of the formula (VI) are: methyl chloride, methyl bromide, methyliudide and acetyl chloride.

The compounds of the formula (IV) are known chemicals.

Process variant (a) according to the invention is preferably carried out in the presence of a diluent. Possible diluents are, in particular, polar solvents, such as, for example, water, methanol, ethanol, n- and iso-propanol, ethylene glycol and its monomethyl ether and dimethyl ether, dioxane, dimethylsulphoxide and dimethylformamide.

Mixtures of water and methanol are particularly preferably used.

Alkali metal hydroxides or alkaline earth metal hydroxides are used for the process - variant (a) -according to the invention. Examples of these are lithium hydroxide, sodium hydroxide, potassium hydroxide, magnesium hydroxide and calcium hydroxide.

Sodium hydroxide and potassium hydroxide are particularly preferably used.

The reaction temperatures can be varied within a substantial range in process (a) according to the invention. The reaction is in general carried out at temperatures between 0° C. and 150° C., preferably at temperatures between 20° C. and 100° C.

Process (a) according to the invention is in general carried out under normal pressure. However, it is also possible for the process to be carried out under increased or reduced pressure.

For carrying out process variant (a) according to the invention, in general between 1 and 3 mol, preferably between 1 and 2 mol, of alkali metal hydroxide or alkaline earth metal hydroxide are employed per mol of starting compound of the formula (II). The reaction components are in general brought together at room temperature and stirred at a somewhat elevated temperature until the reaction has ended.

Work-up can carried out by customary methods; for example by a process in which the mixture is acidified with a dilute aqueous acid, such as, for example, hydrochloric acid, and the product is isolated by filtration with suction and if appropriate purified by recrystallization.

The same diluents as are given above for process (a) are preferably used for process variant (b) according to the invention. Mixtures of water and dimethylsulphoxide are particularly preferred.

The same alkali metal hydroxides and alkaline earth metal hydroxides as are given above for process (a) can likewise be used for process (b). Sodium hydroxide and potassium hydroxide are likewise particularly preferred.

The reaction temperatures can be varied within a substantial range in process (b) according to the invention. The reaction is in general carried out a temperatures between 0° C. and 150° C., preferably at temperatures between 20° C. and 120° C.

Process (b) according to the invention is in general carried out under normal pressure. However, it is also possible for the process to be carried out under increased or reduced pressure.

For carrying out process variant (b) according to the invention, in general between 1 and 5 mol, preferably between 1 and 3 mol, of alkali metal hydroxide or alkaline earth metal hydroxide are employed per mol of starting compound of the formula (III). The reaction and work-up are in general carried out as described above for process (a).

Process (c) according to the invention for the preparation of the new compounds of the formula (Ia) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylenesulphone and hexamethylphosphoric triamide.

All the acid-binding agents which can usually be employed for such reactions can be used as acid acceptors in process (c) according to the invention. Acid acceptors which can preferably be used are alkali metal hydroxides, such as, for example, sodium hydroxide and potassium hydroxide, alkaline earth metal hydroxides, such as, for example, calcium hydroxide, alkali metal carbonates and alcoholates, such as sodium carbonate, potassium carbonate, sodium methylate or ethylate and potassium methylate or ethylate, and furthermore aliphatic, aromatic or heterocyclic amines, for example, triethylamine, trimethylamine, dimethylaniline, dimethylbenzylamine, pyridine, 1,5-diazabicyclo-[4.3.0]non-5-ene (DBN), 1,8-diazabicyclo-[5,4,0]-undec-7-ene (DBU) and 1,4-diazabicyclo-[2,2,2]-octane (DABCO).

If appropriate, process variant (c) according to the invention is carried out in the presence of a metal salt. Metal salts which can be used are, in particular, heavy metal salts, such as, for example, copper sulphate, copper nitrate, silver sulphate, silver nitrate, mercury sulphate and mercury nitrate.

Silver salts, such as, for example, silver nitrate, are particularly preferred.

The reaction temperatures can be varied within a substantial range in process (c) according to the invention. The reaction is in general carried out at temperatures between 0° C. and 100° C., preferably at temperatures between 10° C. and 80° C.

For carrying out process variant (c) according to the invention, the starting substances of the formulae (Ib) and (IV) are in general employed in approximately equimolar amounts. However, the compounds of the formula (IV) can also be used in an excess of up to about 100% without problems. The reaction components are in general brought together at room temperature and if appropriate stirred at elevated temperature until the reaction has ended. Work-up can be carried out by customary methods. For exmaple, the mixture is diluted with an aqueous acid, for example hydrochloric acid—if appropriate after concentration—and extracted with a solvent which is virtually immiscible with water, such as, for example, methylene chloride. The extraction solution is dried—if appropriate after washing with water—and filtered and concentrated. The residue essentially contains the product of the formula (Ia), which can be further purified by customary methods, for example by recrystallization.

The active compounds are suitable for combating animal pests, preferably arthropods and nematodes, in particular arachnida, encountered in agriculture, in forestry, in the protection of stored products and of materials, and in the hygiene field. They are active against normally sensitive and resistant species and against all or some stages of development. The above-mentioned pests include:

From the order of the Isopoda, for example *Oniscus asellus, Armadillidium vulgare* and *Porcellio scaber.*

From the order of the Diplopoda, for example, *Blaniulus guttulatus.*

From the order of the Chilopoda, for exmaple, *Geophilus carpophagus* and Scutigera spec.

From the order of the Symphyla, for example, *Scutigerella immaculata.*

From the order of the Thysanura, for example, *Lepisma saccharina*.

From the order of the collembola, for exmaple, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Salissetial oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blanchardella, Hyponomeuta padella, Plutella maculipennis, Malacosoma neutria, Euproctis chrysorrhoea*, Lymantria spp., *Bucculatrix thurberiella, Phyllocnistic citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatun, Rhizopertha dominica, Acanthoscelides obtectus, Acanthoscelides obtectus, Hylotrupes bajulus, Agelastical alni, Leptinotarsa decemlineata, Phaedon cochleariae*, Diabrotica spp., *Psylliodes chrysocephala, Epiachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxy spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

The active compounds according to the invention exhibit in particular an outstanding acaricidal action, also against resistant spider mites, such as, for example, *Tetranychus urticae*, which damage useful plants, such as, for example, beans.

The active compounds according to the invention exhibit a powerfully microbicidal action and can be used in practice for combating undesirable microorganisms. The active compounds are employed for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention exhibit in particular a powerful fungicidal action, for example a protective action against the apple scab causative organism (*Venturia inaequalis*).

Depending on their particular physical and/or chemical properties, the active compounds can be converted to the customary formulations, such as solutions, emulsions, suspensions, powder, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agent. In the case of the use of water as an extender, organic solvents can, for example, also be used as auxiliary solvents. As liquid solvents, the folowing are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers the following are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules the following are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents the following are suitable: for example nonionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents the following are suitable: for example, lignin-sulphite waste liquors and methylcellulose.

Adhesives such as carboxymethylcellulose and natural and syntheic polymers in the form of powders, granules or latex, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks, etc. in the sectors of animal keeping and cattle breeding; better results, for example higher milk production, greater weight, more attractive animal pelt, longer life, etc., can be achieved by combating the pests.

The application of the active compounds according to the invention occurs in this sector in a known fashion, such as by external application in the form of, for example, dipping, spraying, pouring-on, spotting-on and dusting. The biological effectiveness of the compounds according to the invention will be explained with reference to the examples below.

USE EXAMPLES

The compounds shown below are employed as comparison substances in the use examples which follow:

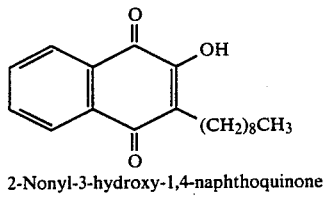

2-Nonyl-3-hydroxy-1,4-naphthoquinone

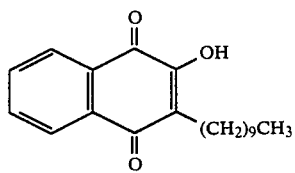

2-Decyl-3-hydroxy-1,4-naphthoquinone

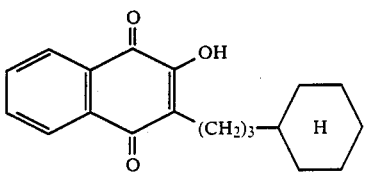

(C)

2-(3-Cyclohexyl-propyl)-3-hydroxy-1,4-naphthoquinone (all known from U.S. Pat. No. 2,572,946).

EXAMPLE A

Tetranychus test (resistant)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed. 0% means that none of the spider mites have been killed.

In this test, for example, the compounds according to the invention listed as examples no. (1), (2), (3), (4), (5) and (9) in Table 1 show a considerably more powerful action than comparison substance (B).

TABLE A (phytopathogenic mites)
Tetranychus test

| Active compound | Active compound concentration in % | Degree of destruction in % after 7 days |
|---|---|---|
| (B) (known) | 0.01 | 0 |
| (1) | 0.01 | 90 |

TABLE A-continued (phytopathogenic mites)
Tetranychus test

| Active compound | Active compound concentration in % | Degree of destruction in % after 7 days |
|---|---|---|
| (5) 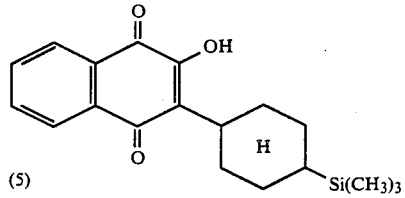 | 0.01 | 65 |
| (2) 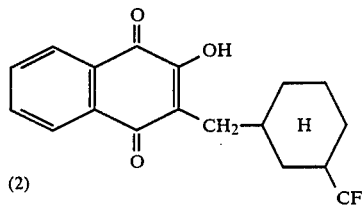 | 0.01 | 98 |
| (3) 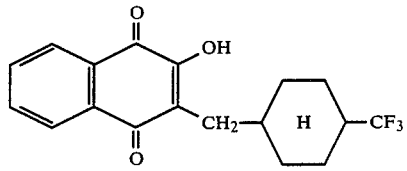 | 0.01 | 100 |
| (4) 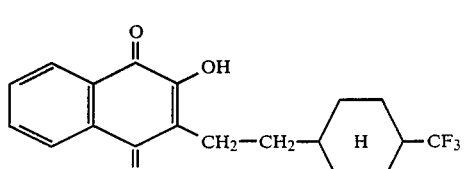 | 0.01 | 100 |
| (9) 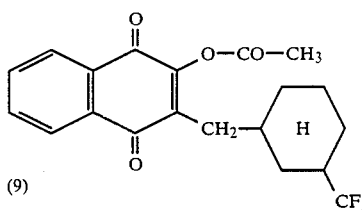 | 0.01 | 100 |

EXAMPLE B

Egg sterility test and development inhibition test with *Tetranychus urticae* (common spider mite)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

The leaves of a bean plant (*Phaseolus vulgaris*) are immersed in the active compound preparation of appropriate concentration. After the preparation of active compound has dried on, the leaves are infested with female spider mites for about 16 hours for eggs to be deposited (about 50 eggs/repeated experiment). The total of sterile and/or destroyed eggs and the destroyed larvae, nymphs and dormant stages of a generation, based on the number of eggs deposited, gives the destruction in %. 100% means that all the animals have been destroyed; 0% means that none of the animals have been destroyed.

In this test, for example, the compounds according to the invention listed as examples no. (6), (7), and (9) in Table 1 show a considerably more powerful action than comparison compounds (A), (B) and (C).

TABLE B (phytopathogenic mites)
Tetranychus test

| Active compound | Active compound concentration in % | Degree of destruction in % after 14 days |
|---|---|---|
| (A) naphthoquinone-OH with $(CH_2)_8CH_3$ (known) | 0.01 | 0 |
| (B) naphthoquinone-OH with $(CH_2)_9CH_3$ (known) | 0.01 | 0 |
| (C) naphthoquinone-OH with $(CH_2)_3$–cyclohexyl-H (known) | 0.01 | 40 |
| (9) naphthoquinone-O–CO–CH$_3$ with CH$_2$–cyclohexyl(H)–CF$_3$ | 0.01 | 100 |
| (6) naphthoquinone-OH with CH$_2$–cyclohexyl(H)–CF$_3$ | 0.01 | 100 |
| (7) naphthoquinone-OH with CH$_2$–CH$_2$–cyclohexyl(H)–SCF$_3$ | 0.01 | 100 |

EXAMPLE C

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative humidity for 1 day.

The plants are then placed in a greenhouse at 20° C. and a relative humidity of about 70%.

Evaluation is carried out 12 days after the inoculation.

In this test, a clearly superior activity compared with the prior art is shown, for example, by the compounds listed as an example no. (2), (3) and (5) in Table 1.

TABLE C

Venturia test (apple) / protective

| Active compound | Infestation in % at an active compound concentration of 10 ppm |
|---|---|
| (B) 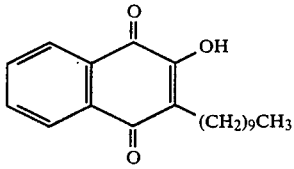 (known) | 44 |
| (C) 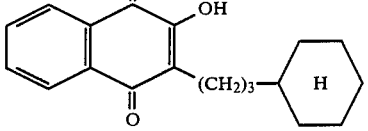 (known) | 17 |
| (3) 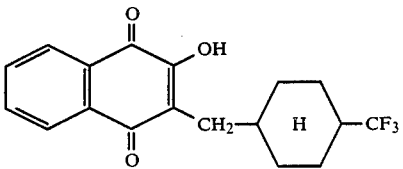 | 0 |
| (2) 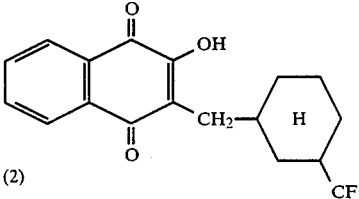 | 0 |

TABLE C-continued

Venturia test (apple) / protective

| Active compound | Infestation in % at an active compound concentration of 10 ppm |
|---|---|
| (5) 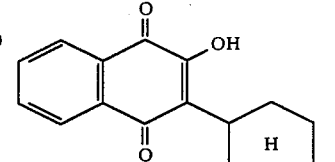 | 3 |

EXAMPLE D

Test with *Psoroptes ovis*

Solvent: 35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the desired concentration.

About 10-25 *Psoroptes ovis* are introduced into 1 ml of the active compound preparation to be tested, which had been pipetted into tablet nests of a deep-drain package. The degree of destruction is determined after 24 hours.

In this test, a very powerful action is shown for example, by the compounds listed as examples (1), (2), (3), (4), (5) and (7) in Table 1.

TABLE D

Psoroptes ovis test

| Active compound | Active compound concentration [ppm of active ingredient] | Destructive action in % Psoroptes ovis |
|---|---|---|
| (1) 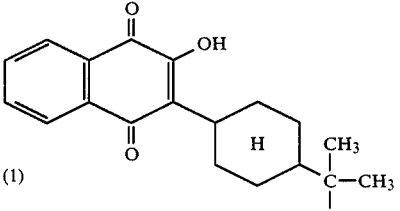 | 10<br>3<br>1<br>0.3<br>0.1<br>0.03<br>0.01<br>0.003 | 100<br>100<br>100<br>100<br>100<br>100<br>100<br>0 |
| (2) 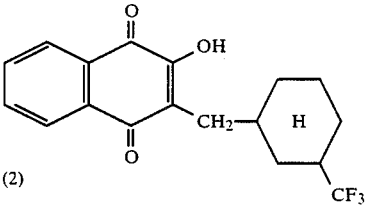 | 10<br>3<br>1 | 100<br>100<br>100 |

TABLE D-continued

Psoroptes ovis test

| Active compound | Active compound concentration [ppm of active ingredient] | Destructive action in % Psoroptes ovis |
|---|---|---|
| 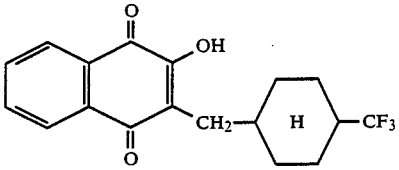 (3) | 10<br>3<br>1<br>0.3 | 100<br>100<br>100<br>0 |
| 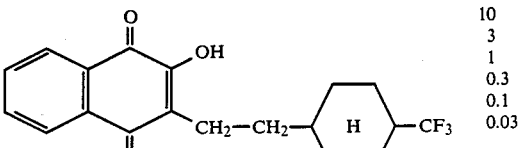 (4) | 10<br>3<br>1<br>0.3<br>0.1<br>0.03 | 100<br>100<br>100<br>100<br>100<br>0 |
| 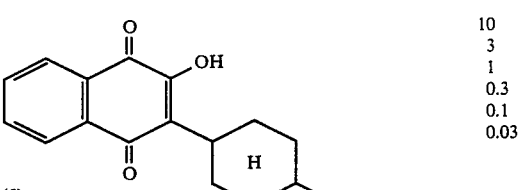 (5) | 10<br>3<br>1<br>0.3<br>0.1<br>0.03 | 100<br>100<br>100<br>100<br>100<br>0 |
| 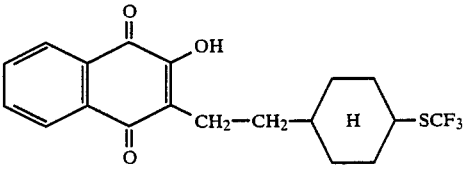 (7) | 10<br>3<br>1 | 100<br>100<br>100 |

Preparation Examples

EXAMPLE 1

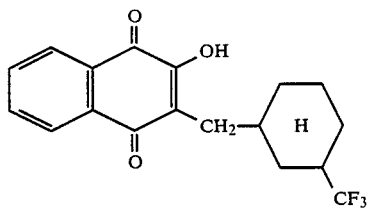

A mixture of 22 g (0.062 mol) of 3-chloro-2-(3-trifluoromethyl-1-cyclohexyl-methyl)-1,4-naphthoquinone, 5.2 g (0.09 mol) of potassium hydroxide, 50 ml of methanol and 50 ml of water is heated under reflux at the boiling point for 60 minutes. After cooling, the mixture is acidified with 2N hydrochloric acid and the product is filtered off with suction and recrystallized from isopropanol.

15 g (72% of theory) of 2-(3-trifluoromethyl-1-cyclohexyl-methyl)-3-hydroxy-1,4-naphthoquinone of melting point 142° C. are obtained.

EXAMPLE 2

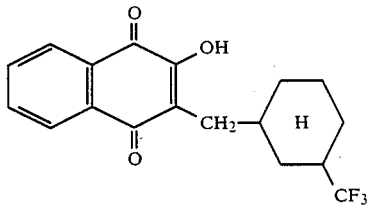

A mixture of 10 g (0.03 mol) of 2,3-epoxy-2,3-dihydro-2-(3-trifluoromethyl-1-cyclohexylmethyl)-1,4-naphthoquinone, 5 g (0.09 mol) of potassium hydroxide, 15 ml of water and 85 ml of dimethylsulphoxide is stirred at 100° C. for 60 minutes. After cooling, the mixture is neutralized with 2N hydrochloric acid and the product is filtered off with suction.

8.3 g (83% of theory) of 2-(3-trifluoromethyl-1-cyclohexyl-methyl)-3-hydroxy-1,4-naphthoquinone of melting point 142° C. are obtained.

The compounds of the formula (I) listed as Examples No. 1, 3, 4, 5, 6, 7 and 8 in Table 1 can also be prepared analogously to Preparation Examples 1 and 2 which lead to the compound listed as Example 2 in Table 1.

EXAMPLE 3

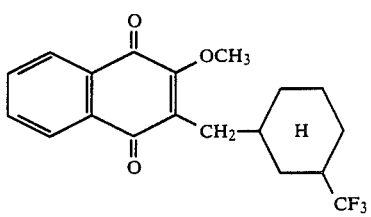

2.8 g (0.02 mol) of iodomethane are added dropwise to a mixture of 3.4 g (0.01 mol) of 2-(3-trifluoromethyl-1-cyclohexyl-methyl)-3-hydroxy-1,4-naphthoquinone, 1.38 g (0.01 mol) of potassium carbonate, 1.69 g (0.01 mol) of silver nitrate and 50 ml of acetone, with stirring, and the reaction mixture is stirred under reflux for 6 hours. It is then acidified with 2N hydrochloric acid and filtered and the filtrate is extracted with methylene chloride. The solvent is distilled off from the extract and the residue is recrystallized from isopropanol.

2.8 g (88% of theory) of 2-(3-trifluoromethyl-1-cyclohexyl-methyl)-3-methoxy-1,4-naphthoquinone of melting point 90° C. (compare Example No. 15 in Table 1) are obtained.

EXAMPLE 4

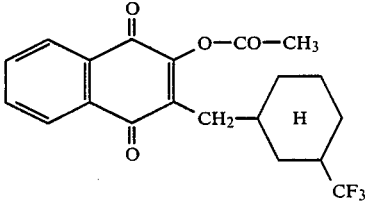

2.0 g (0.026 mol) of acetyl chloride are added dropwise to a mixture of 8.5 g (0.025 mol) of 2-(3-trifluoromethyl-1-cyclohexyl-methyl)-3-hydroxy-1,4-naphthoquinone, 3.0 g (0.03 mol) of triethylamine and 50 ml of methylene chloride, with stirring, and the reaction mixture is stirred at 20° C. for 2 hours. It is then acidified with 2N hydrochloric acid, the organic phase is separated off and the solvent is distilled off therefrom under reduced pressure.

8.74 g (92% of theory) of 2-(3-trifluoromethyl-1-cyclohexyl-methyl)-3-acetoxy-1,4-naphthoquinone are obtained as a crystalline residue of melting point 110° C. (compare Example No. 9 in Table 1).

The compounds of the formula (I) listed as Examples No. 10, 11, 12, 13, 14, 16, 17, 18, 19, 20 and 21 in Table 1 can also be prepared analogously to Preparation Examples 3 and 4 - which lead to the compounds listed as Example No. 15 or 9 in Table 1.

Starting substances of the formula (II)

EXAMPLE (II-1)

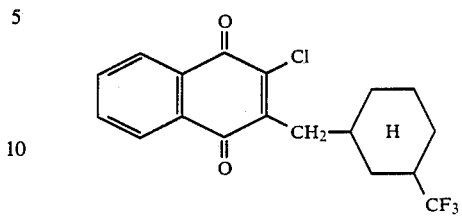

A mixture of 15 g (0.078 mol) of 2-chloro-1,4-naphthoquinone, 21.3 g (0.1 mol) of (3-trifluoromethylcyclohexyl)-acetic acid, 4.5 g (0.027 mol) of silver nitrate, 100 ml of acetonitrile and 50 ml of sulpholane is heated to 65° C. A solution of 26.3 g (0.115 mol) of ammonium peroxodisulphate in water is added dropwise at this temperature in the course of 30 minutes and the reaction mixture is stirred at this temperature for a further 30 minutes. It is then poured onto ice and the product is isolated by filtration with suction and recrystallized on isopropanol/water.

13.5 g (53% of theory) of 2-chloro-3-(3-trifluoromethyl-1-cyclohexyl-methyl)-1,4-naphthoquinone of melting point 104° C. are obtained.

Starting substances of the formula (III)

EXAMPLE (III-1)

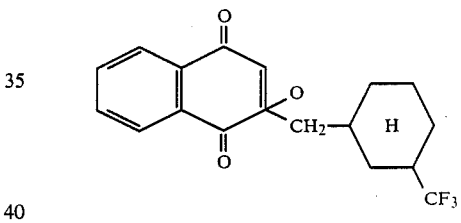

A mixture of 8 g (0.025 mol) of 2-(3-trifluoromethyl-1-cyclohexyl-methyl)-1,4-naphthoquinone, 2.7 g (0.025 mol) of sodium carbonate, 6.5 ml of 30% strength aqueous hydrogen peroxide (corresponding to 0.057 mol of $H_2O_2$) and 100 ml of dioxane is stirred at 70° C. for 10 minutes. After cooling, the mixture is diluted with water and the product obtained as crystals is isolated by filtration with suction.

7.4 g (88% of theory) of 2,3-epoxy-2,3-dihydro-2-(3-trifluoromethyl-1-cyclohexyl-methyl)-1,4-naphthoquinone of melting point 85° C. are obtained.

Starting substances of the formula (VII)

EXAMPLE (VII-1)

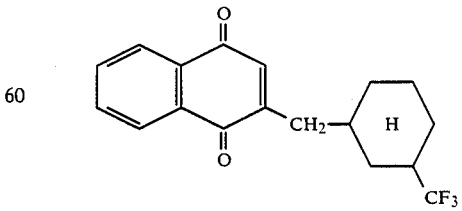

15.8 g (0.1 mol) of 1,4-naphthoquinone, 27.3 g (0.13 mol) of (3-trifluoromethyl-cyclohexyl)-acetic acid and 5.7 g (0.03 mol) of silver nitrate are mixed in with 150 ml of water and 150 ml of acetonitrile and the mixture is heated to 65° C. 34.2 (0.15 mol) of ammonium peroxodisulphate are added dropwise as an aqueous solution at this temperature in the course of 30 minutes, with stirring. The reaction mixture is stirred at 65° C. for a further 30 minutes and is then poured onto ice. The product is isolated by filtration with suction and purified by chromatography on silica gel (with methylene chloride/cyclohexane).

27.4 g (85% of theory) of 2-(3-trifluoromethyl-1-cyclohexyl-methyl)-1,4-naphthoquinone of melting point 65° C. are obtained.

It will be appreciated that the instant specification and claims are set forth by way of illustration and not limitation, and that various modifications and changes may be made without departing from the spirit and scope of the present invention.

What is claimed is:

1. A method of combating agricultural pests comprising applying a pesticidally effective amount of a substituted 1,4-naphthoquinone on agricultural pests and/or their environment, said 1,4-naphthoquinone being of the formula

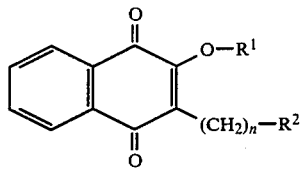

in which
n represents the numbers zero, 1 or 2,
$R^1$ represents hydrogen, t-butylcarbonyl or acetyl and
$R^2$ represents phenyl which is substituted by bromine, fluorine, chlorine, [$C_1$-$C_4$-alkyl,] trifluoromethyl, trifluoromethoxy, trifluoromethylsulphenyl, trifluoromethylsulphonyl or trimethylsilyl or cyclohexyl which is substituted by methyl, trifluoromethyl or trimethylsilyl or $R^2$ represents $C_1$-$C_8$-alkyl which is substituted by fluorine, chlorine or bromine.

2. A method according to claim 1 wherein the pest is arachnida.

3. A method according to claim 1 wherein the pest is fungi.

4. A method according to claim 1, wherein the substituted 1,4-naphthoquinone is selected from the group consisting of

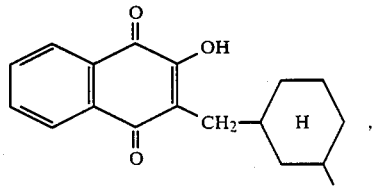

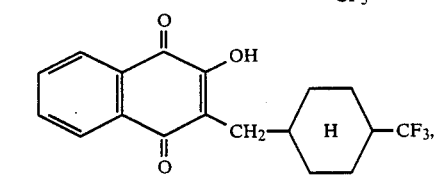

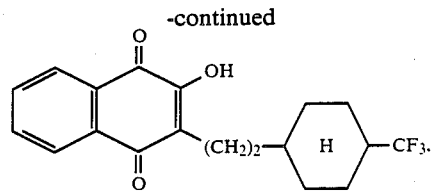

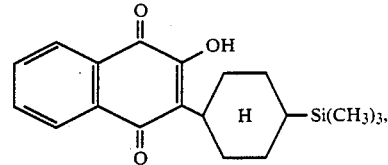

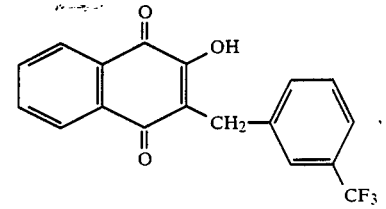

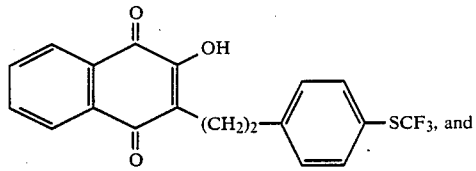

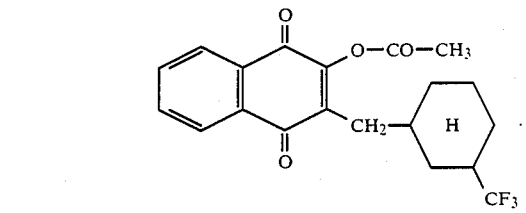

5. A substituted 1,4-naphthoquinone of the formula

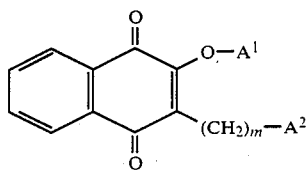

in which
m represents the number 0 or a number from 1 to 12,
$A^1$ represents hydrogen, methyl, benzyl, acetyl, methoxycarbonyl, benzenesulphonyl or toluenesulphonyl and
$A^2$ represents trifluoromethyl, 3-trifluoromethyl-cyclohexyl, 3-trifluoromethyl-phenyl, 4-trimethylsilyl-cyclohexyl or 4-trifluoromethylthiophenyl, with the proviso that m is other than 0 and 2 if $A^2$ represents 3-trifluoromethyl-cyclohexyl or 3-trifluoromethyl-phenyl.

6. A substituted 1,4-naphthoquinone according to claim 5, wherein
m represents the number zero or a number from 1 to 10,
$A^1$ represents hydrogen, methyl, acetyl or benzyl and
$A^2$ represents trifluoromethyl, 3-trifluoromethyl-cyclohexyl, 3-trifluoromethyl-phenyl, 4-trifluoromethylsilyl-cyclohexyl or 4-trifluoromethylthio-phenyl, with the proviso that m is other than zero and 2 if $A^2$ represents 3-trifluoromethyl-cyclohexyl or 3-trifluoromethyl-phenyl.

* * * * *